(12) United States Patent
Braido et al.

(10) Patent No.: US 11,986,386 B2
(45) Date of Patent: *May 21, 2024

(54) LEAFLET IN CONFIGURATION FOR FUNCTION IN VARIOUS SHAPES AND SIZES

(71) Applicant: St. Jude Medical, Cardiology Division, Inc., St. Paul, MN (US)

(72) Inventors: Peter N. Braido, Wyoming, MN (US); Katherine A. Ahmann, Arden Hills, MN (US); Mina S. Fahim, Shoreview, MN (US); Jeffrey J. Allison, Mayer, MN (US); Andrea L. McCarthy, Vadnais Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 678 days.

This patent is subject to a terminal disclaimer.

(21) Appl. No.: 16/907,917

(22) Filed: Jun. 22, 2020

(65) Prior Publication Data
US 2020/0315793 A1   Oct. 8, 2020

Related U.S. Application Data

(63) Continuation of application No. 15/376,905, filed on Dec. 13, 2016, now Pat. No. 10,722,350, which is a
(Continued)

(51) Int. Cl.
*A61F 2/24* (2006.01)

(52) U.S. Cl.
CPC .......... *A61F 2/2418* (2013.01); *A61F 2/2412* (2013.01); *A61F 2220/005* (2013.01);
(Continued)

(58) Field of Classification Search
None
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 A1 | 11/2002 |

(Continued)

OTHER PUBLICATIONS

Ruiz, Carlos, Overview of PRE-CE Mark Transcatheter Aortic Valve Technologies, Euro PCR—dated May 25, 2010?
(Continued)

*Primary Examiner* — Leslie A Lopez
(74) *Attorney, Agent, or Firm* — SLEMAN & LUND LLP

(57) ABSTRACT

A prosthetic heart valve includes a collapsible and expandable stent having a proximal end, a distal end, an annulus section adjacent the proximal end and an aortic section adjacent the distal end. The heart valve further includes a plurality of commissure features disposed on the stent, and a collapsible and expandable valve assembly, the valve assembly including a plurality of leaflets connected to the plurality of commissure features, each of the plurality of leaflets having a free edge and being configured to have a tension line aligned near the free edge to prevent backflow.

20 Claims, 17 Drawing Sheets

Related U.S. Application Data continuation of application No. 13/781,423, filed on Feb. 28, 2013, now Pat. No. 9,554,902.

(60) Provisional application No. 61/665,616, filed on Jun. 28, 2012.

(52) U.S. Cl.
CPC ............... *A61F 2220/0066* (2013.01); *A61F 2220/0075* (2013.01); *A61F 2250/0017* (2013.01); *F04C 2270/0421* (2013.01)

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Etendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,329,278 B2 | 2/2008 | Seguin et al. | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 2002/0036220 A1 | 3/2002 | Gabbay | |
| 2002/0072794 A1* | 6/2002 | Gabbay ................ A61F 2/2412 623/2.11 |
| 2002/0173842 A1 | 11/2002 | Buchanan | |
| 2003/0023303 A1 | 1/2003 | Palmaz et al. | |
| 2003/0027332 A1* | 2/2003 | Lafrance ............ A61L 27/3843 435/366 |
| 2003/0050694 A1 | 3/2003 | Yang et al. | |
| 2003/0078652 A1 | 4/2003 | Sutherland | |
| 2003/0114913 A1 | 6/2003 | Spenser et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0110439 A1 | 6/2004 | Chaikof et al. | |
| 2004/0186563 A1 | 9/2004 | Lobbi | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0206202 A1 | 9/2006 | Bonhoeffer et al. | |
| 2006/0235511 A1 | 10/2006 | Osborne | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2006/0276888 A1* | 12/2006 | Lee ..................... A61F 2/2412 623/2.14 |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0103586 A1 | 5/2008 | Styrc et al. | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147179 A1 | 6/2008 | Cai et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0228264 A1 | 9/2008 | Li et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |

(56) References Cited

U.S. PATENT DOCUMENTS

| | | |
|---|---|---|
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0238167 A1 | 9/2011 | Dove et al. |
| 2011/0282440 A1 | 11/2011 | Cao et al. |
| 2012/0123529 A1* | 5/2012 | Levi .................. A61F 2/2433 623/2.11 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0062716 A1 | 10/2000 |
| WO | 0128459 A1 | 4/2001 |
| WO | 200149213 A3 | 7/2001 |
| WO | 0154625 A1 | 8/2001 |
| WO | 0156500 A2 | 8/2001 |
| WO | 2001076510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 2007071436 A2 | 6/2007 |
| WO | 08070797 A2 | 6/2008 |
| WO | 2008101083 A2 | 8/2008 |
| WO | 2009042196 A2 | 4/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012082952 A2 | 6/2012 |

OTHER PUBLICATIONS

Quaden et al., "Percutaneous aortic valve replacement: resection before implantation", pp. 836-840, European J. of Cardio-thoracic Surgery, 27 (2005).

Catheter-implanted prosthetic heart valves, Knudsen, L.L., et al., The International Journal of Artificial Organs, vol. 16, No. 5 1993, pp. 253-262.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Braido et al., U.S. Appl. No. 29/375,243, filed Sep. 20, 2010, titled "Surgical Stent Assembly".

U.S. Appl. No. 29/375,260, filed Sep. 20, 2010.

International Search Report & Written Opinion for Application No. PCT/US2013/048132 dated Jan. 29, 2014.

Liu, et al , "Effect of fiber orientation on the stress distribution within a leaflet of a polymer composite heart valve in the closed position", Journal of Biomechanics, v.40(5), pp. 1099-1106.

International Euopean Search Report for Application No. 13737065 dated Mar. 12, 2019.

* cited by examiner

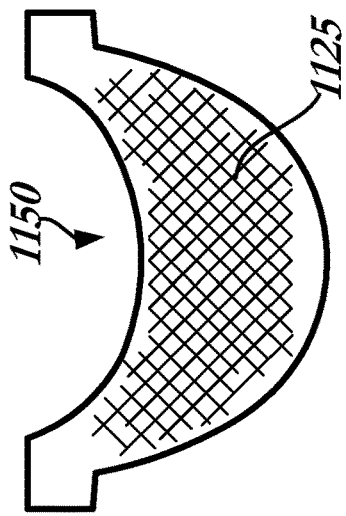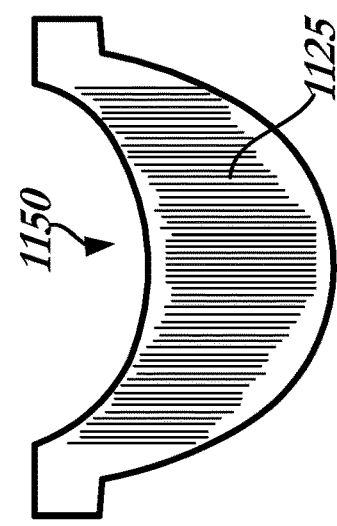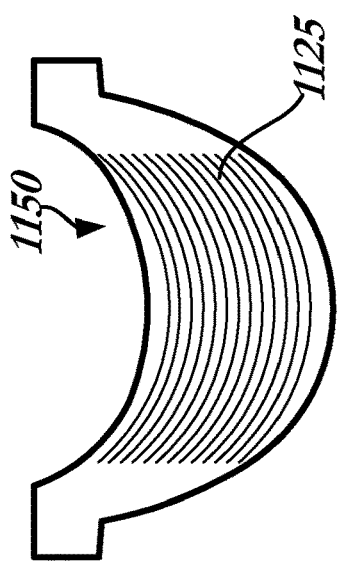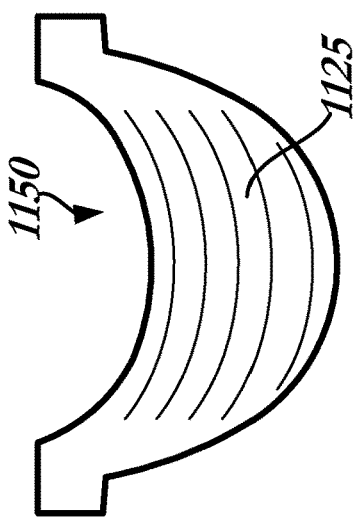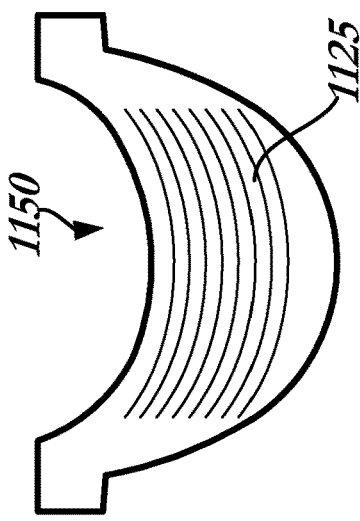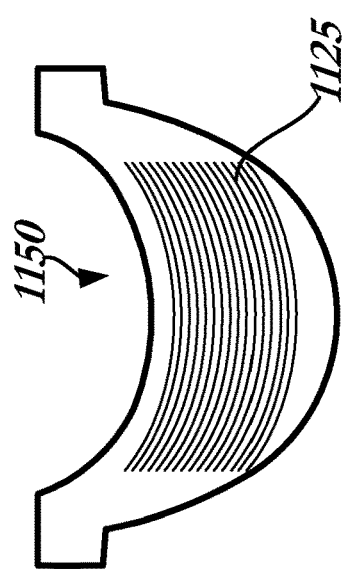

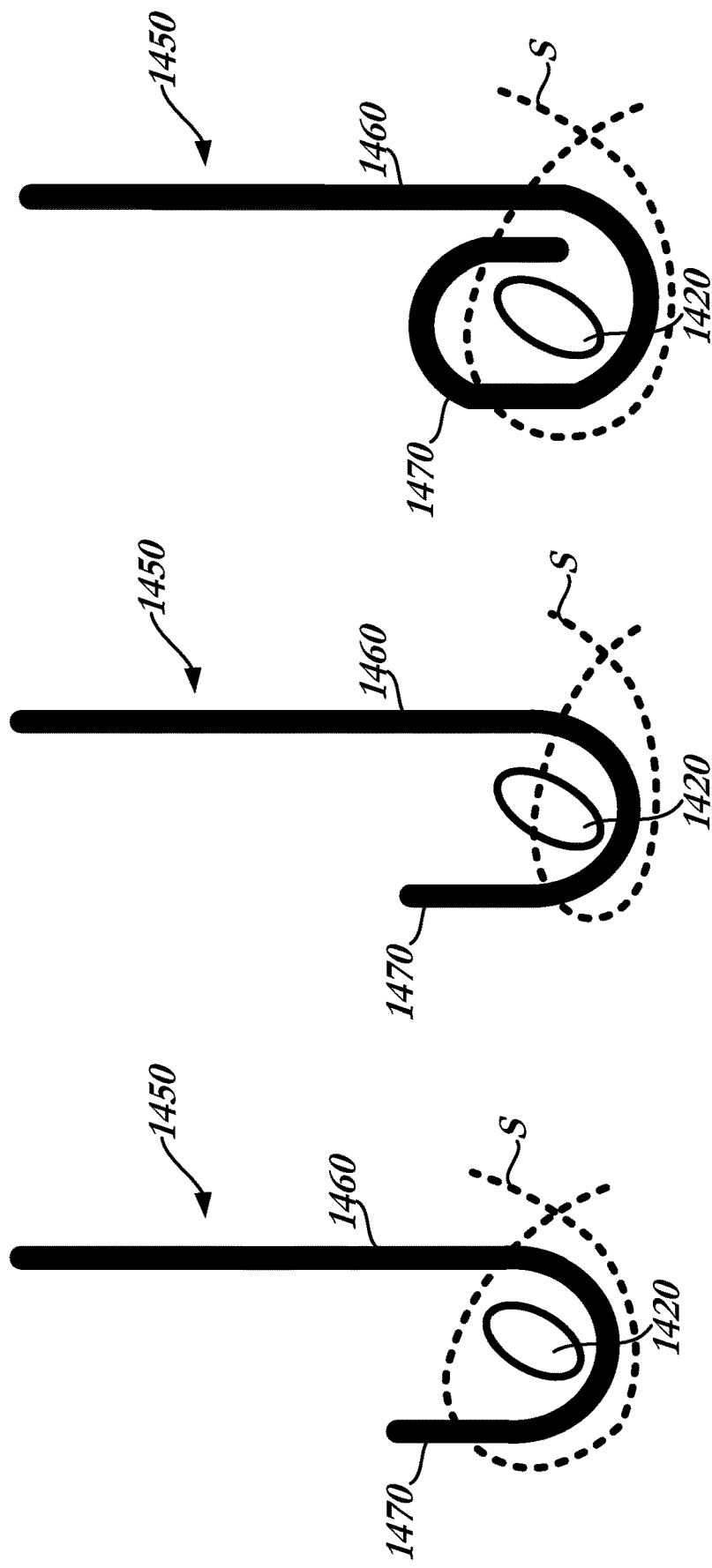

LEAFLET IN CONFIGURATION FOR FUNCTION IN VARIOUS SHAPES AND SIZES

CROSS REFERENCE TO RELATED APPLICATIONS

This application is a continuation of U.S. application Ser. No. 15/376,905, filed on Dec. 13, 2016, which is a continuation of U.S. application Ser. No. 13/781,423, filed on Feb. 28, 2013, now U.S. Pat. No. 9,554,902, which claims the benefit of the filing date of U.S. Provisional Patent Application No. 61/665,616 filed Jun. 28, 2012, the disclosures of which are hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having superior leaflet performance.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Despite the various improvements that have been made to the collapsible prosthetic heart valve delivery process, conventional delivery devices, systems, and methods suffer from some shortcomings. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency cannot be treated well, if at all, with the current collapsible designs.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

SUMMARY OF THE INVENTION

In some embodiment, a prosthetic heart valve includes a collapsible and expandable stent having a proximal end, a distal end, an annulus section adjacent the proximal end and an aortic section adjacent the distal end. A plurality of commissure features is disposed on the stent. The valve further includes a collapsible and expandable valve assembly, the valve assembly including a plurality of leaflets connected to the plurality of commissure features, each of the plurality of leaflets having a free edge and a belly portion, and being configured to have a tension line aligned between the free edge and the belly portion to prevent backflow.

In some examples, the plurality of leaflets is capable of coapting along a coaptation axis, the coaptation axis being substantially aligned with a force vector from an applied back pressure.

In some embodiments, a prosthetic heart valve includes a collapsible and expandable stent having a proximal end, a distal end, an annulus section adjacent the proximal end and an aortic section adjacent the distal end. A plurality of commissure features is disposed on the stent. The heart valve further includes a collapsible and expandable valve assembly, the valve assembly including a plurality of leaflets connected to the plurality of commissure features, each of the plurality of leaflets having a free edge, a belly portion and fibers configured and arranged to provide adequate coaptation.

In some examples, the fibers are arranged in a circumferential orientation, the fibers traversing the leaflets parallel to the free edge and the belly portion. The fibers may be arranged in an axial orientation, the fibers extending from the free edge to the belly portion of each leaflet or may be randomly oriented.

In some examples, the maximum difference in deflection values between any two of the plurality of leaflets under the same load may be from about 0 to 1.0 mm under a load of 250 KPa. The maximum deflection value for each of the plurality of leaflets may be from about 1.0 to about 5.0 mm under a load of 250 KPa.

In some embodiments a prosthetic heart valve includes a collapsible and expandable stent having a proximal end, a distal end, an annulus section adjacent the proximal end and an aortic section adjacent the distal end. A plurality of commissure features may be disposed on the stent. The heart valve may further include a collapsible and expandable valve assembly, the valve assembly including a plurality of leaflets connected to the plurality of commissure features, each of the plurality of leaflets having a body portion, a foldover portion and a reinforcement coupled to at least one of the body portion and the foldover portion.

In some examples, the reinforcement may include a cord or a strip of fabric. The reinforcement may be coupled to the leaflet using a suture. The suture may begin at a first side of the leaflet, passes through the body portion, over the reinforcement, through the foldover portion, and forms a loop to end back at the first side of the leaflet. The suture may also begin at a first side of the leaflet, and passes through the body portion, the reinforcement, and the foldover portion in a loop. The foldover portion may wrap around the reinforcement and the suture begins at a first side of the leaflet, passes through the body portion, through the foldover portion, through the foldover portion a second time, and forms a loop to end back at the first side of the leaflet. The suture may form a whip stitch around the reinforcement and the leaflet.

In at least some embodiments, a leaflet for a collapsible and expandable valve assembly includes a belly portion having a first edge adapted to couple to at least one of a stent or a cuff, the belly portion having an area of reduced thickness. The leaflet may further include a free edge opposite the first edge adapted to coapt with free edges of other leaflets and at least one tab adapted to couple the leaflet to a commissure feature of the stent.

In some examples, the area of reduced thickness may be disposed in the center of the belly portion. The area of reduced thickness may include multiple areas of reduced thickness disposed in regions of low stress. The area of reduced thickness may include two areas of reduced thickness. The area of reduced thickness may be formed by laser milling, cryocutting, or trimming a segment of the belly portion.

BRIEF DESCRIPTION OF THE DRAWINGS

Various embodiments of the presently disclosed heart valve are disclosed herein with reference to the drawings, wherein:

FIGS. 11A-C are diagrammatic plan views of leaflets having various fiber orientations;

FIGS. 11D-F are diagrammatic plan views of leaflets having various fiber densities;

FIGS. 14A-C are diagrammatic views showing various configurations of incorporating reinforcement into a leaflet belly;

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
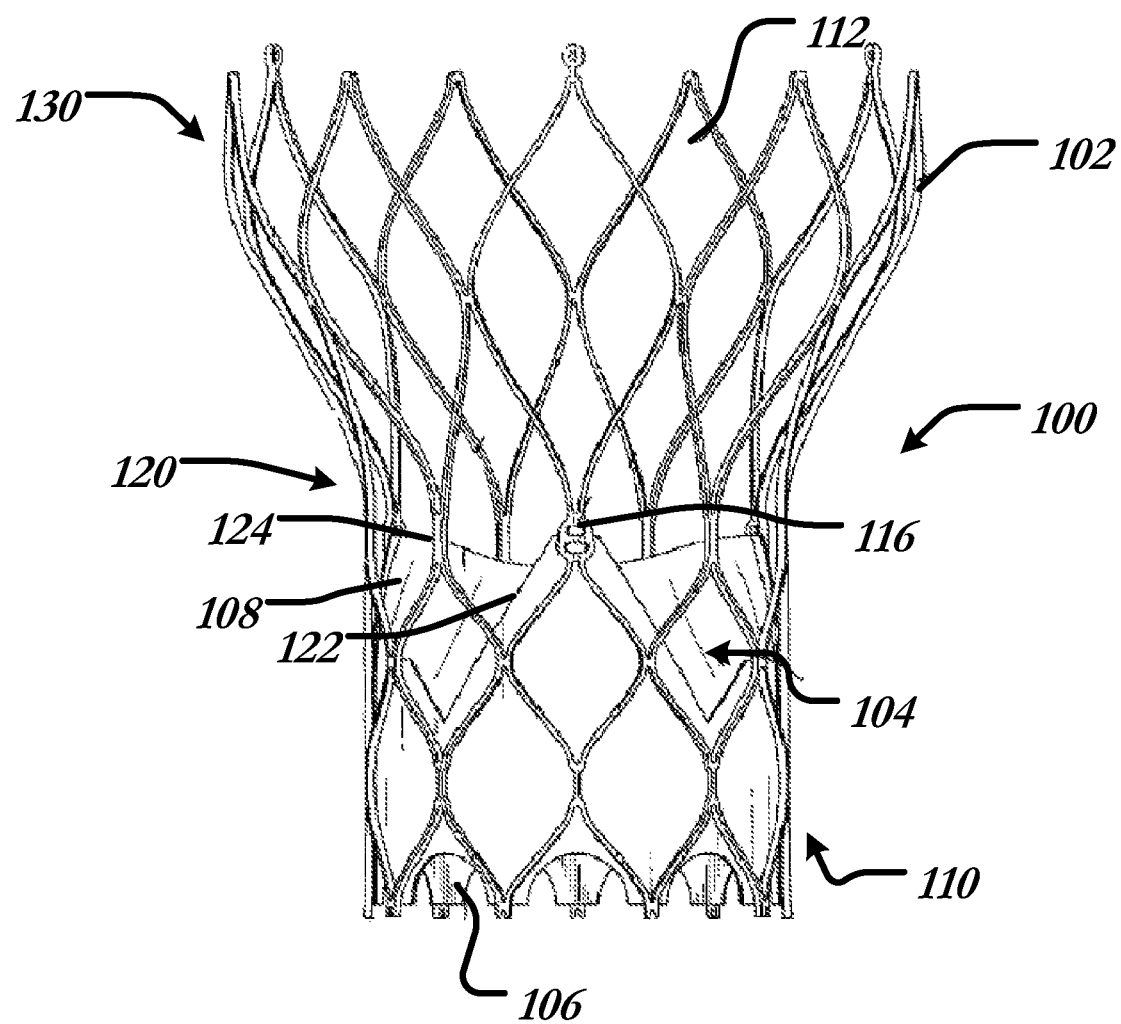
FIG. 1 is a partial side elevational view of a prosthetic heart valve including a valve assembly and a stent.

FIG. 1 shows a collapsible prosthetic heart valve 100 according to an embodiment of the present disclosure. The prosthetic heart valve 100 is designed to replace the function of a native aortic valve of a patient. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110, a transition section 120 and an aortic section 130. Each of the annulus section 110 and the aortic section 130 of the stent 102 includes a plurality of cells 112 connected to one another around the stent. The annulus section 110 and the aortic section 130 of the stent 102 may each include one or more annular rows of cells 112 connected to one another. For instance, the annulus section 110 may have two annular rows of cells 112. When the prosthetic heart valve 100 is in the expanded condition, each cell 112 may be substantially diamond shaped.

The stent 102 may include commissure features 116 connecting at least two cells 112 in the longitudinal direction of the stent 102. The commissure features 116 support the ends of valve leaflets, as will be described more fully below.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester. In some embodiments, the cuff and/or the sutures may include ultra-high-molecular-weight polyethylene.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. FIG. 1 shows cuff 106 disposed on the lumenal surface of annulus section 110 so as to cover part of the annulus section while leaving another part thereof uncovered. The valve assembly 104 may further include a plurality of leaflets 108 which collectively function as a one-way valve. A first edge 122 of each leaflet 108 may be attached to the stent 102 by any suitable attachment means, such as suturing, stapling, adhesives or the like. For example, the first edge 122 of each leaflet 108 may be sutured to the stent 102 by passing strings or sutures through the cuff 106 of the valve assembly 104. A second or free edge 124 of each leaflet 108 may coapt with the corresponding free edges of the other leaflets, thereby enabling the leaflets to function collectively as a one-way valve.

In operation, the prosthetic heart valve 100 may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device, including the delivery devices described in detail below. During delivery, the prosthetic heart valve is disposed inside the delivery device in the collapsed condition. The delivery device may be introduced into a patient using a transfemoral, transapical or transseptal approach, or any other minimally invasive technique. Once the delivery device has reached the target site, the user may deploy any of the prosthetic heart valves described above. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

In certain procedures, collapsible valves may be implanted in a native valve annulus without first resecting the native valve leaflets. Implantation in this manner may result in critical clinical issues because of the nature of the stenotic leaflets that are left in place. It will also be appreciated that the wide range of variables in patients with uneven calcification, bi-cuspid aortic valve disease, and/or valve insufficiency makes the treatment of these patients difficult.

The reliance on evenly calcified leaflets could lead to several problems such as: (1) perivalvular leakage (PV leak), (2) valve migration, (3) mitral valve impingement, (4) conduction system disruption, (5) coronary blockage, etc., all of which can have severely adverse clinical outcomes. To reduce these adverse events, the optimal valve would seal and anchor adequately without the need for excessive radial force, protrusion into the left ventricular outflow tract (LVOT), etc., that could harm nearby anatomy and physiology.

Figure 2A:
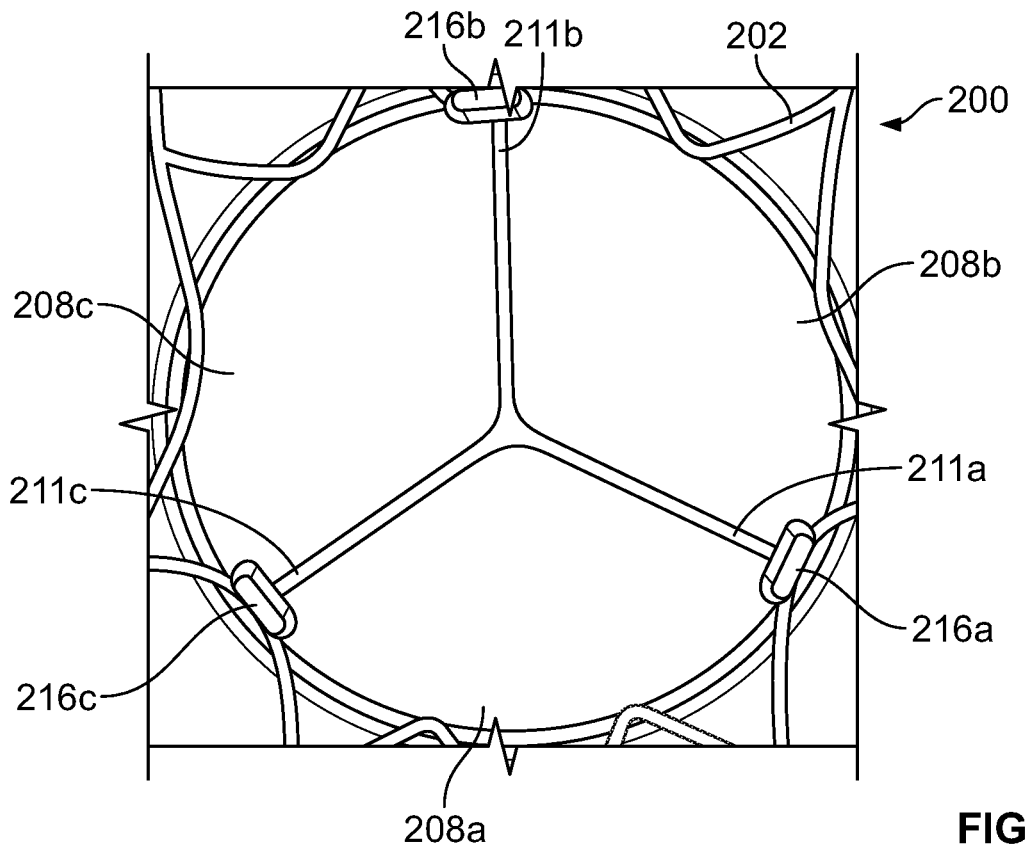
FIG. 2A is an end view of the prosthetic heart valve of FIG. 1 implanted in a patient and viewed from the outflow region toward the heart and the native valve annulus, the valve assuming a circular configuration.
Figure 2B:
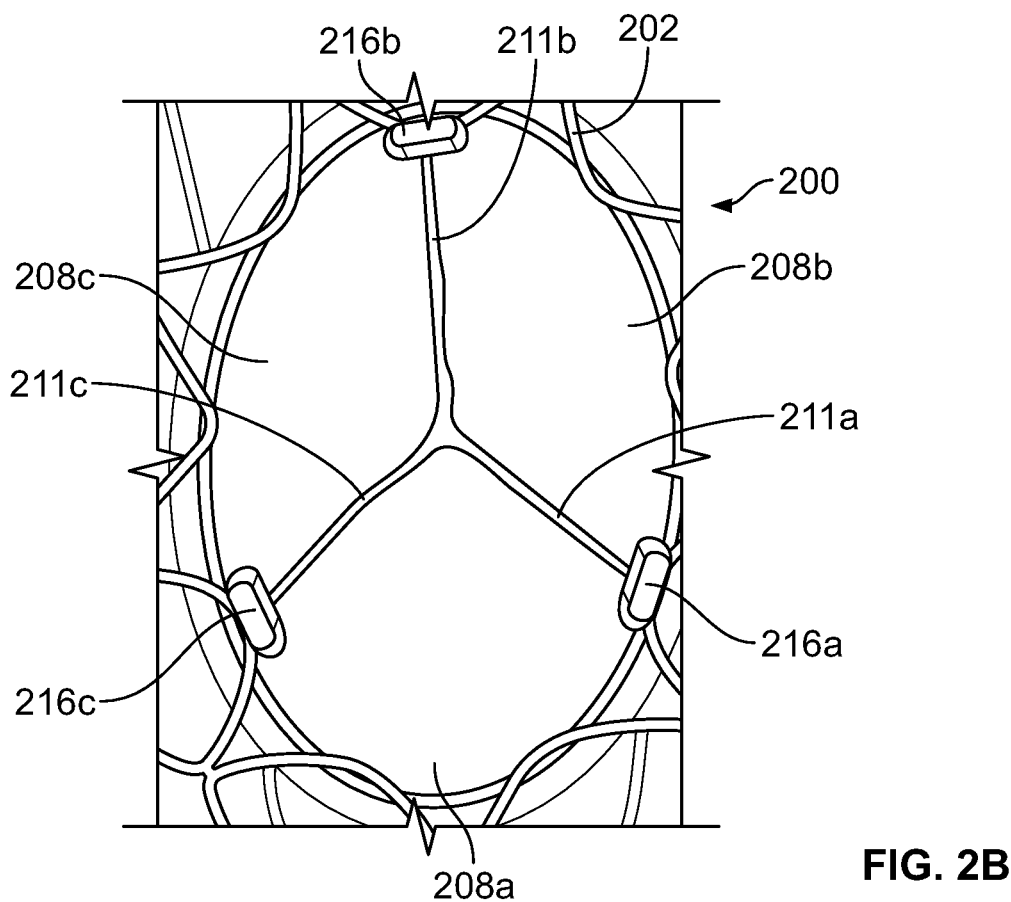
FIG. 2B is an end view of the prosthetic heart valve of FIG. 1 implanted in a patient and viewed from the aortic sinus toward the heart and the native valve annulus, the valve assuming an elliptical configuration.

FIGS. 2A and 2B show an end view of an implanted prosthetic valve 200 as seen from the downstream side of the valve assembly, e.g., looking from the aorta or aortic sinus toward the heart and the native valve annulus when implanted in the aortic valve. As seen in FIG. 2A, the valve assembly includes valve leaflets 208a, 208b, and 208c attached a stent 202. At least one edge of each leaflet 208 is sutured to the stent 202 and to two of three commissure features 216a-c, leaving at least one edge free to move in response to the pumping of blood. As the blood pressure in the left ventricle increases, the free edges of the leaflets move away from one another to allow blood to flow from the left ventricle to the aorta, following which the free edges move toward one another and coapt to prevent blood from flowing back from the aorta into the left ventricle.

It will be understood that the coaptation of "the free edges" of the valve leaflets does not necessarily mean that the actual edges meet per se. Indeed, the leaflets are preferably sized, shaped, and attached such that a suitable "belly" contour is formed. And each leaflet should include a portion extending from the free edge toward the annulus (referred to herein as a "coaptation section") that may engage the coaptation sections of the other leaflets such that there will be a surface area of contact between the leaflets rather than edge-to-edge contact. This surface area of contact is important so that, when in a closed or "coapted" condition, the leaflets cooperate to substantially prevent backflow or regurgitation of blood through the valve. These areas of actual contact between the coaptation sections of adjacent leaflets are referred to herein as the coaptation junctions of the leaflets and are illustrated in FIG. 2A at 211a, 211b, and 211c. The coaptation section of each leaflet may range in size as a particular valve design demands, but generally will be sufficient in size to provide some tolerance, or the ability to form a coaptation junction even if the shape of the valve is distorted during placement, as illustrated in FIG. 2B.

The annulus section of prosthetic valve 200 has a generally regular cylindrical shape by which is meant that the section has a generally circular cross-section with a substantially constant diameter along its length. When placed in the annulus of a native heart valve, such as, for example, the tricuspid aortic valve, and expanded, a substantially fluid-tight fit should result. However, the native valve annulus may not be circular, and, in fact, its shape may vary from patient to patient, as may the shape of the aortic sinus or aorta, the angle of the junction between the valve annulus and the aortic sinus, and other local anatomical features. When prosthetic valve 200 is deployed and expanded, it must accommodate these anatomical variations in order to function properly. This may result in a distortion in the shape of stent 202 and/or valve assembly 204, and the repositioning of leaflets 208a, 208b, and 208c relative to one another, which can affect the coaptation junctions 211a, 211b, and 211c.

As the stent of a collapsible prosthetic heart valve distorts during implantation, during beating of the heart, or because of irregularities in the patient's anatomy or the condition of the native valve, such distortion may be translated to the valve assembly, such that not all of the valve leaflets meet to form effective coaptation junctions. This can result in leakage or regurgitation and other inefficiencies which can reduce cardiac performance. Moreover, if the prosthetic valve is not placed optimally and the valve leaflets are not coapting as intended, other long term effects, such as uneven wear of the individual leaflets, can be postulated.

As shown in FIG. 2B, ideally, valve leaflets 208a, 208b, and 208c fully coapt despite the distortion of the annulus section of the stent 202 (hidden behind the valve leaflets in this figure) into a more elongated or elliptical configuration. As will be appreciated, the distortion of the annulus section affects the relative positions of commissure features 216a-c, as well as the positions of leaflets 208a-c relative to one another. The ability of the valve leaflets 208a-c to fully coapt despite this distortion enables prosthetic valve 200 to function in the manner intended.

Figure 3A:
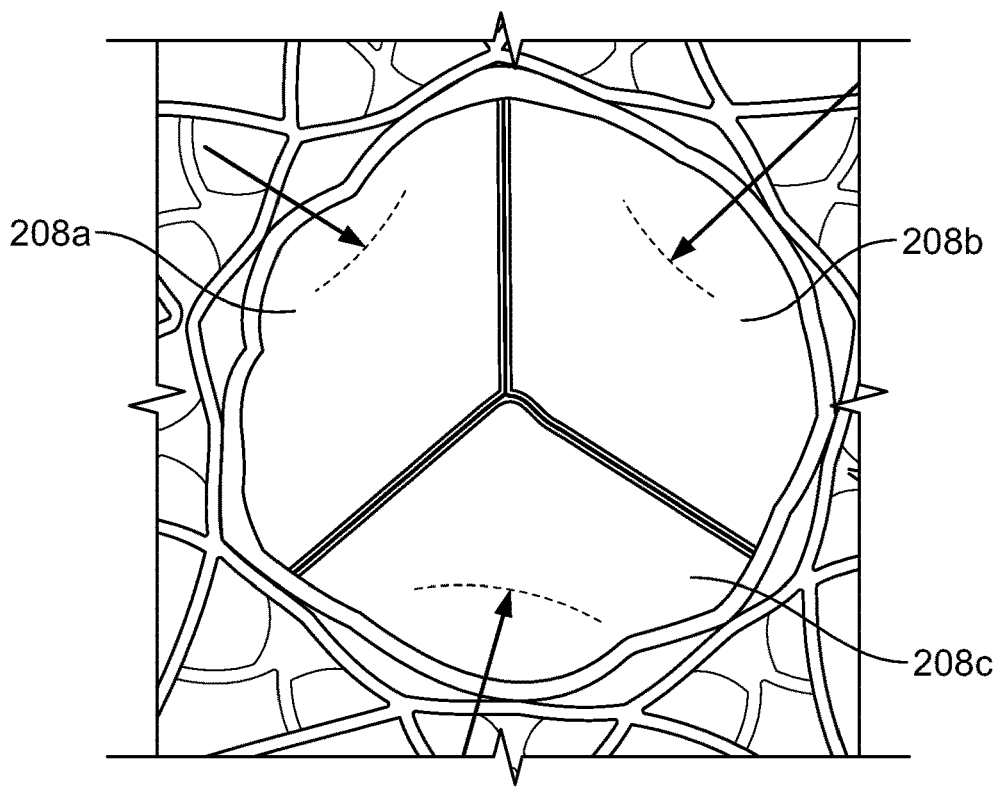
FIGS. 3A and 3B are end views of the prosthetic heart valve of FIG. 1 implanted in a patient and viewed from the aortic sinus toward the heart and the native valve annulus, the valve assuming other configurations due to anatomical differences.
Figure 3B:
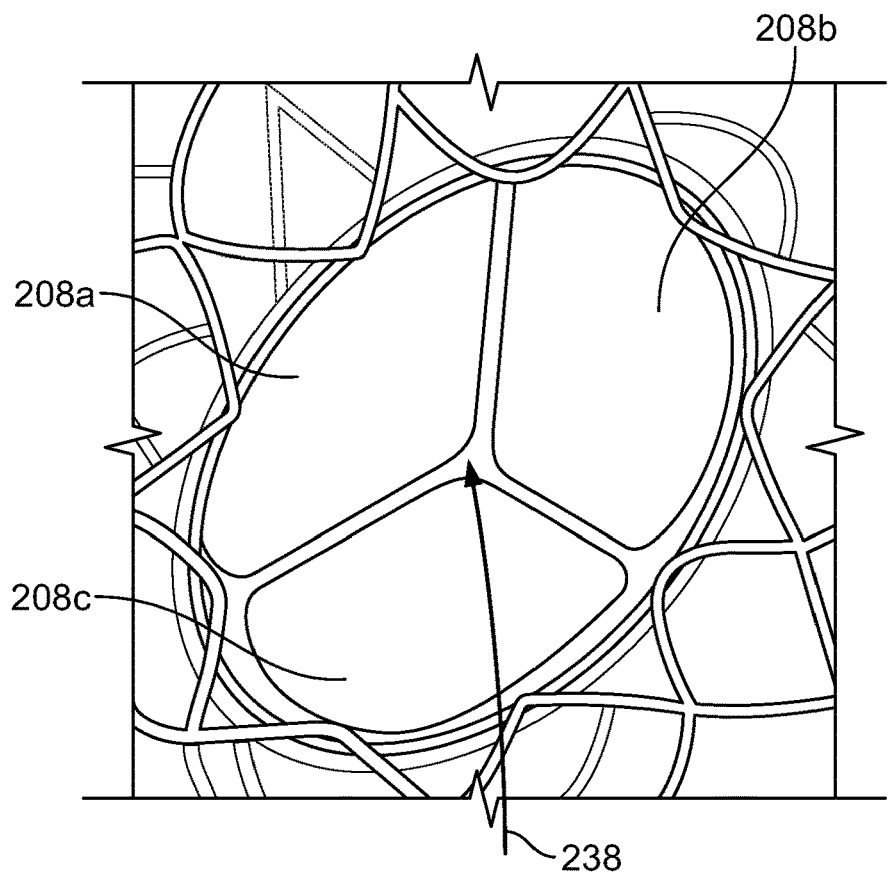

FIGS. 3A and 3B illustrate a pair of prosthetic valves 200 as seen from the downstream side of the valve assembly, e.g., looking from the aorta or aortic sinus toward the heart and the native valve annulus, disposed in elliptical configurations. As seen in FIGS. 3A and 3B, imperfect geometry may result in inferior performance of conventional valves. FIG. 3A, for example, illustrates creasing of the valve leaflets. Creasing may lead to more wear and less durability of the leaflets. FIG. 3B illustrates inadequate coaptation of the leaflets 208a-c. Specifically, the leaflets 208 of a conventional device are incapable of complete coaptation when disposed in a native valve annulus with an elliptical, ovoid or otherwise non-circular configuration. In some examples, prolapsing of a leaflet may result in a gap 238 formed between the leaflets 208. Such inadequate coaptation may lead to leakage and regurgitation as discussed above.

The present invention addresses at least some of these issues. It is noted that while the inventions herein described are predominately discussed in terms of a tricuspid valve and a stent having a shape as illustrated in FIG. 1, the valve could be a bicuspid valve, such as the mitral valve, and the stent could have different shapes, such as a flared or conical annulus section 110, a less-bulbous aortic section 130, and the like, and a differently shaped transition section 120.

Figure 4:
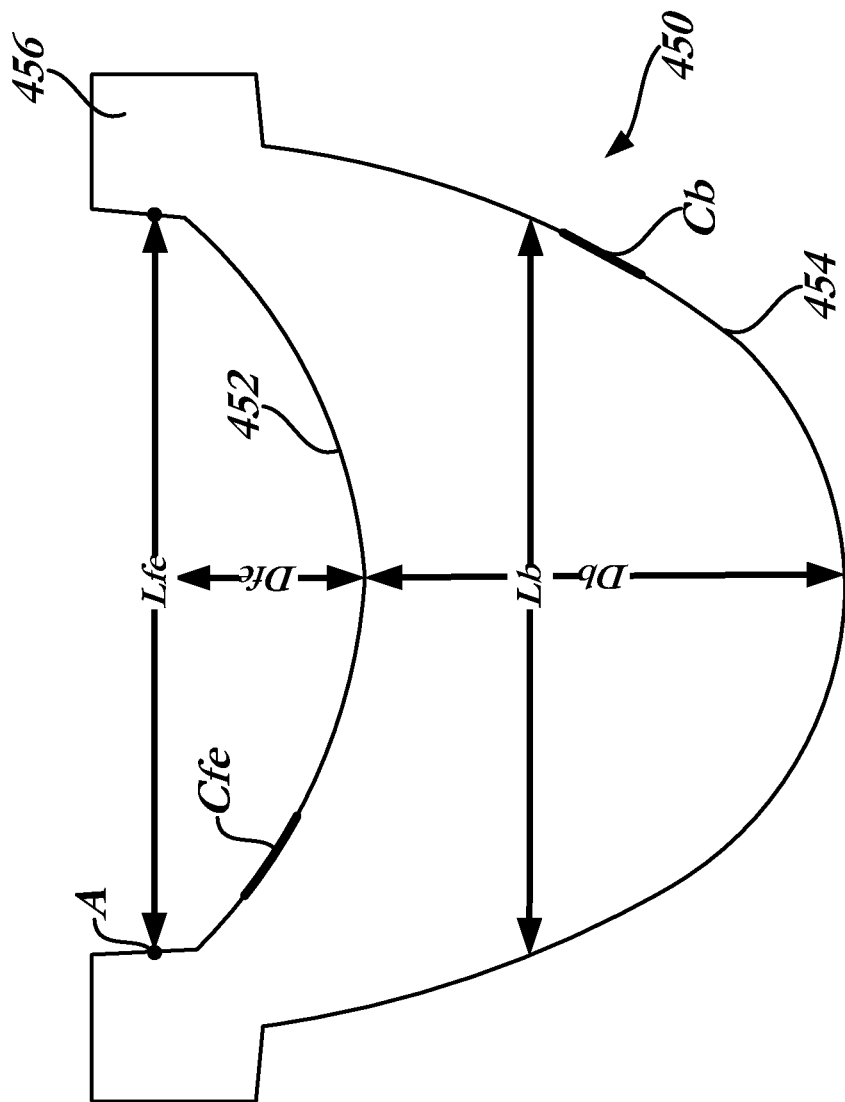
FIG. 4 is a plan view of one embodiment of a leaflet having a free edge, a belly and tabs for attaching to a commissure feature.

The leaflets may be constructed to mitigate some of the problems discussed above and to yield additional benefits. FIG. 4 illustrates a leaflet 450 having a free edge 452 for coapting with other leaflets, a belly 454 and tabs 456 for attaching to a commissure feature. Two leaflets 450 may be attached to each other and to a commissure feature at tabs 456.

In order to describe the features of the present invention, several geometric parameters and dimensions will be defined with reference to FIG. 4. The free edge 452 of each leaflet may have a curved free edge contour Cfe. As seen in FIG. 4, free edge contour Cfe may vary along the length of the free edge. The bottom belly portion may include a belly contour Cb which likewise varies in curvature along its length. In addition to these curvatures, the dimensions of leaflet 450 may be varied to modify function. Free edge 452 has a free edge length Lfe, defined as the distance between attachment points "A" at tabs 456, and a free edge depth Dfe defined as the distance between the attachment point "A" and the center of free edge 452. Likewise, belly 454 may have a belly length Lb, defined as the varying distance from one side of belly 454 to the opposite side, and a belly depth Db, defined as the distance between free edge 452 and the bottom of belly 454 as seen in FIG. 4. It should be understood that changing any one of these dimensions may effect a change in another dimension or set of dimensions. For example, changing the belly depth Db may affect the belly contour Cb.

Figure 5:
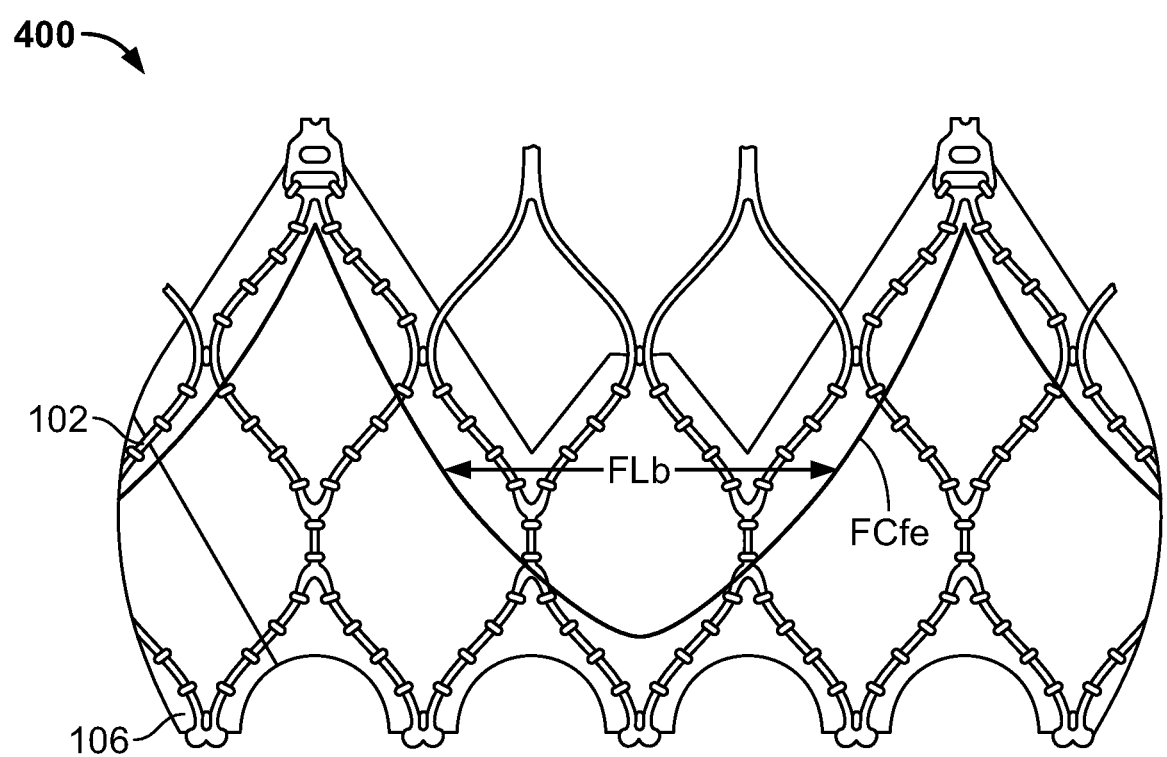
FIG. 5 is a developed view showing the attachment of a leaflet to a prosthetic valve assembly.

FIG. 4 illustrates leaflet 450 via two-dimensional geometry. It will be understood, however, that when attaching leaflet 450 to other leaflets to form a valve assembly, the resulting structure has a three-dimensional geometry that results in additional considerations. FIG. 5 illustrates a leaflet 450 attached to a prosthetic valve assembly 400. In assembly, certain portions of leaflet 450 also do not naturally align with the stent 102 and/or cuff 106, and the operator will suture such leaflet portions in place, either stretching the material or creating some slack. Thus, when assembled to the stent 102, the leaflet dimensions may be said to be "forced" into place. The amount of forcing may depend on the intended outcome. For example, the amount of forcing may result in a valve with higher or lower resheath forces or increased coaptation. This is because when a belly is forced either circumferentially or axially along the belly contour it translates into a change of where the bulk of the leaflet resides in three dimensions. If, for example, the leaflet belly is forced to be closer to a ring in the same circumferential plane the bulkiness when crimped would be very high near that plain. If the leaflet is pulled to be in a very acute V-shape, the free edge may be pulled so low that it could not have enough material to reach the central axis where the leaflets meet.

A few additional dimensions will be defined in order to differentiate between the unassembled and assembled dimensions of the leaflets. As used herein, the forced belly length FLb refers to the distance from one side of belly 454 to the opposite side after assembly, and the forced belly depth FDb refers to the distance between free edge 452 and the bottom of belly 454 after assembly. The prosthetic valve 400 will further include a forced free edge contour FCfe after assembly.

Figure 6:
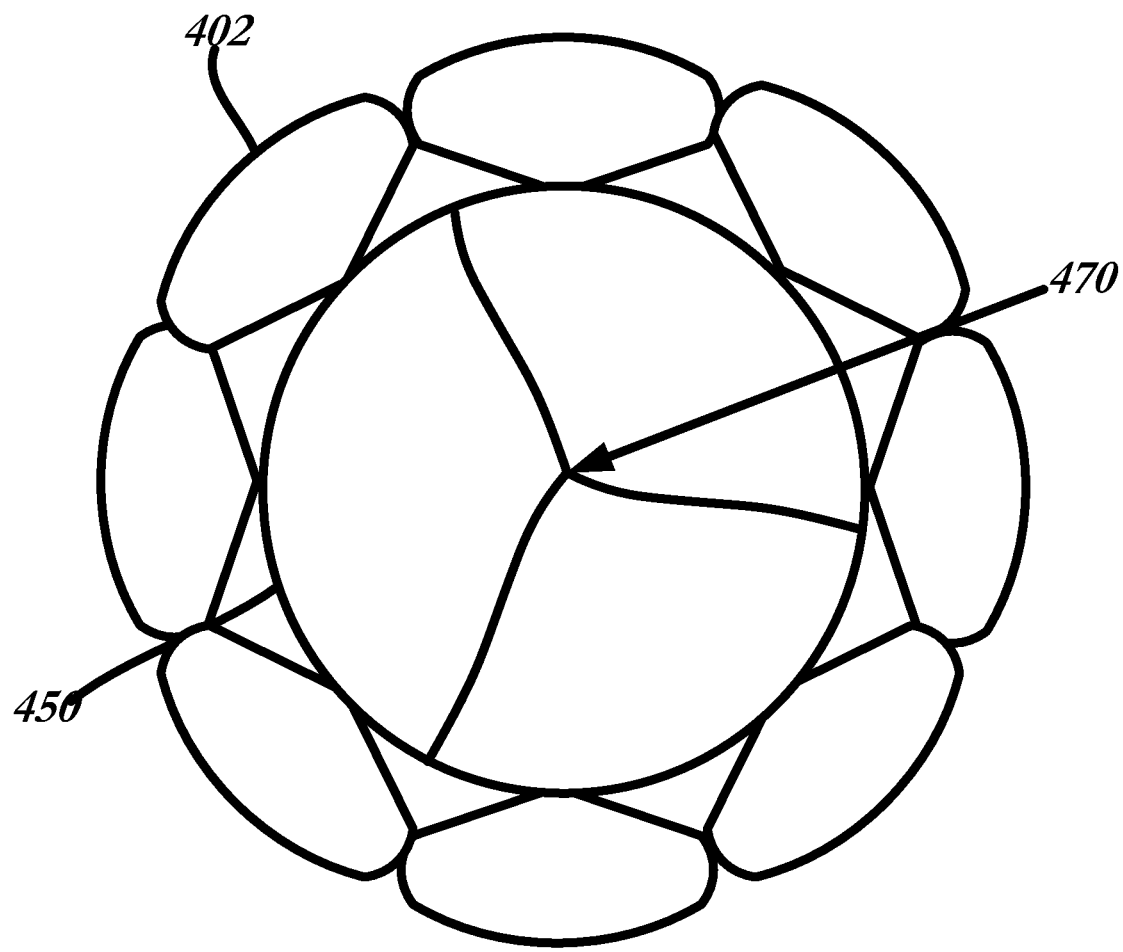
FIG. 6 is an end view of a prosthetic heart valve showing leaflet coaptation.

FIG. 6 illustrates a properly functioning valve assembly including a plurality of leaflets 450 attached to a stent 402. As will be appreciated from FIG. 6, successful design, manufacture and assembly of leaflets 450 results in proper coaptation of all three leaflets 450 at a triple point 470 under backpressure.

Figure 7:
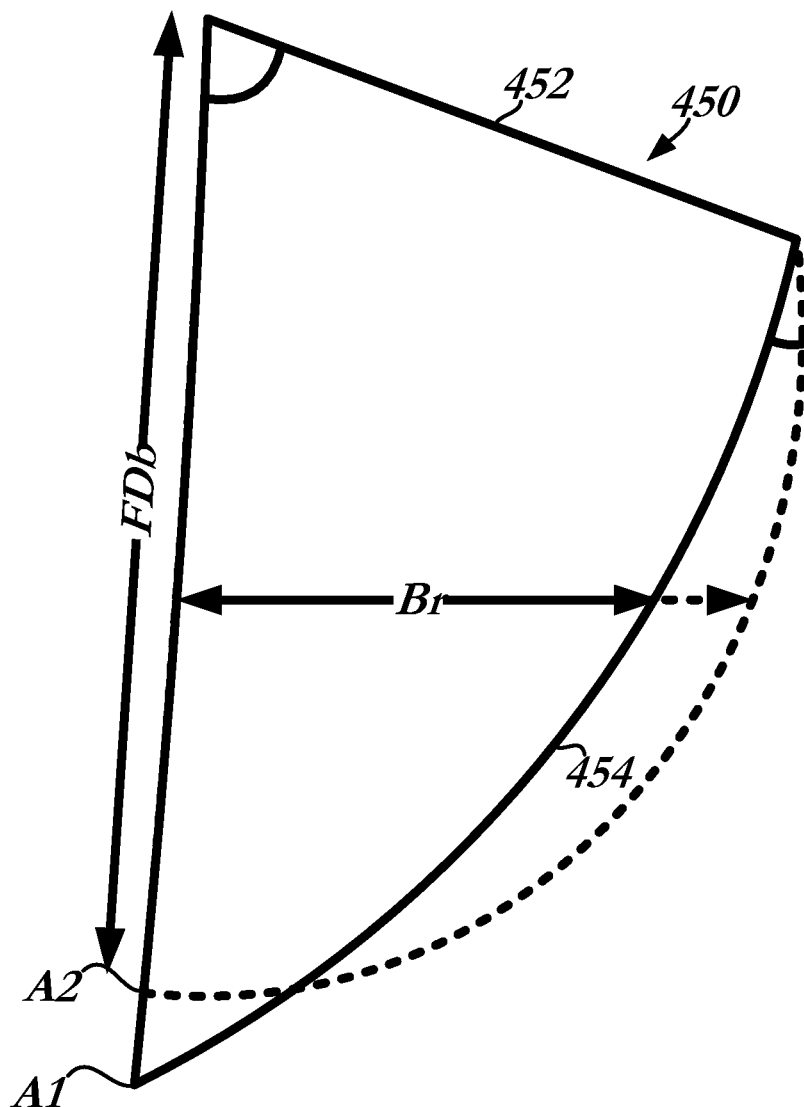
FIG. 7 is a diagrammatic view of a portion of a leaflet showing the effects of changing the forced belly length on the three-dimensional leaflet shape.
Figure 8:
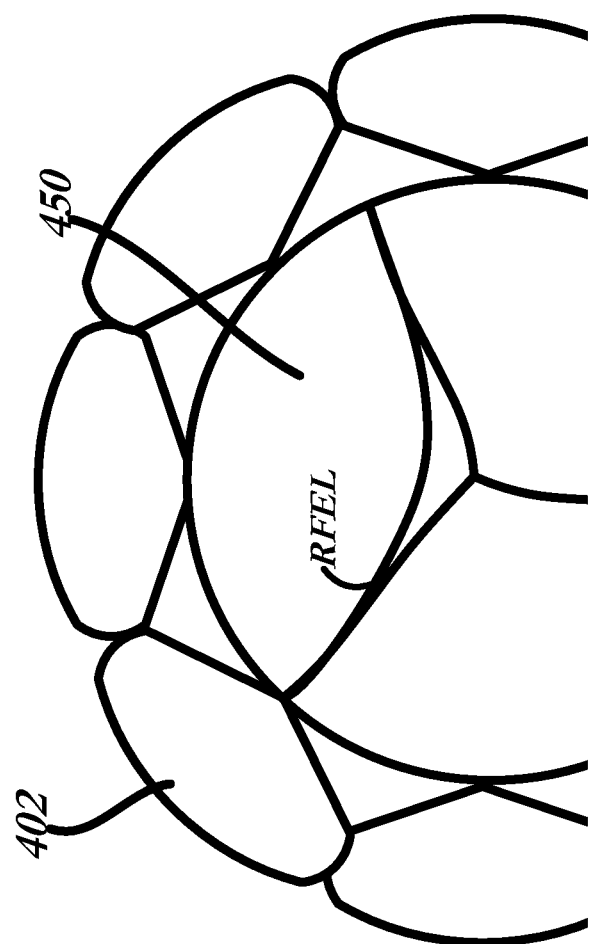
FIG. 8 is a partial end view of a prosthetic heart valve showing the effects of changing the forced belly length on the three-dimensional leaflet shape.

The effects of changing the forced belly depth FDb on the three-dimensional leaflet shape will be discussed with reference to FIGS. 7 and 8. Leaflet 450 may include a free edge 452 and a belly 454 as discussed above. Specifically, FIG. 7 illustrates the effects of changing the forced belly depth FDb on the belly radius Br and belly contour. Br is a function of FDb and FLb and is zero along the belly attachment to cuff/stent. In a first example, leaflet 450 is attached to the stent at point A1 and the forced belly depth FDb results in a belly radius Br. If the belly attachment point is raised along the stent from point A1 to point A2, the forced belly depth FDb is decreased and the three-dimensional belly radius Br will increase as the leaflet 450 will not be as tight and will result in the rounding out of the three-dimensional belly contour.

The RFEL may be defined as the chord length of the free edge as taken thru the plane at the level of the triple point. As seen in FIG. 8, as the forced belly depth FDb is decreased, the resting free edge length RFEL will be increased to shift the triple point coaptation axis and the amount of coaptation area.

Figure 9:
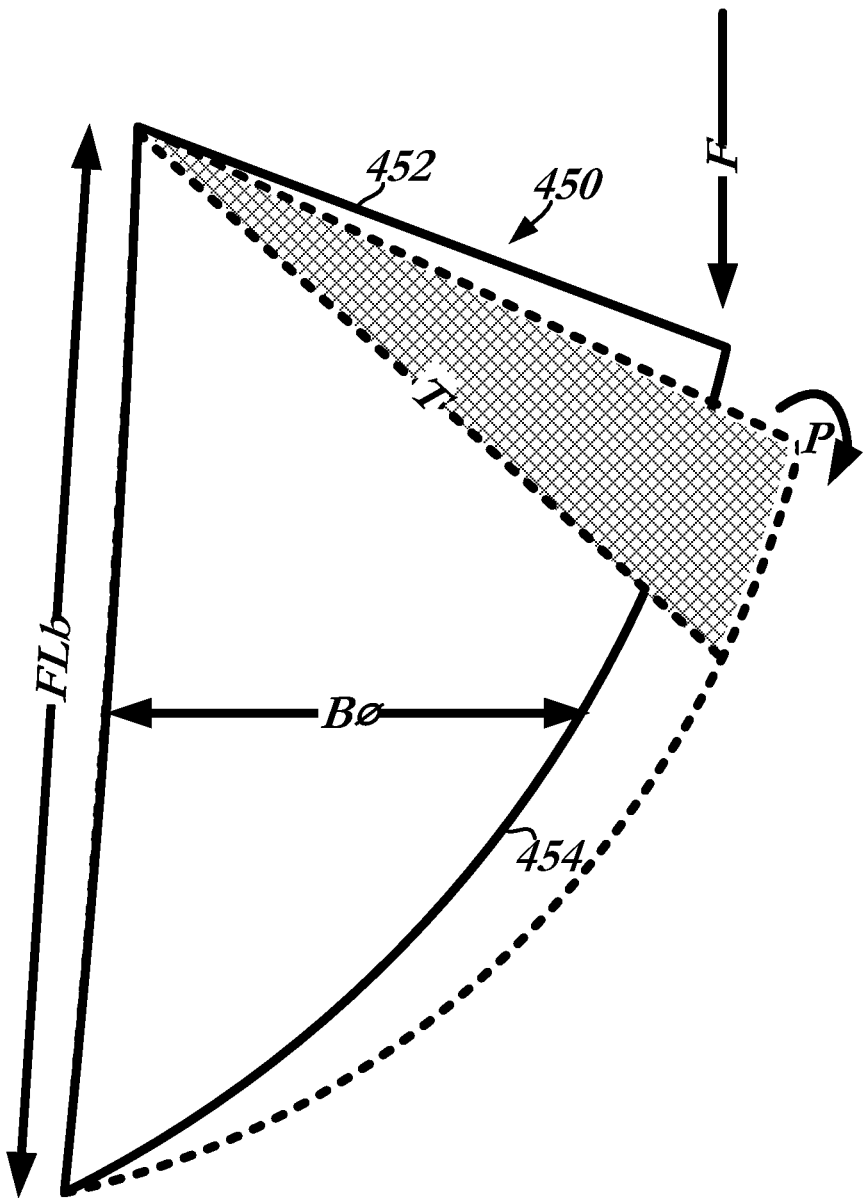
FIG. 9 is a diagrammatic view of a portion of a leaflet showing the effects of applying a force to its free edge.

As previously discussed, altering any one of the leaflet dimensions is likely to impact other dimensions. FIG. 9 illustrates a leaflet 450 having a free edge 452 and a belly before and after a force F has been applied to its free edge. The resting position of leaflet 450 is shown in solid lines, and the leaflet 450 is shown in dashed lines after a force has been applied to the free edge. In the aortic valve position for example, such force may be applied by the back pressure of blood in the aorta after the left ventricle has contracted. If leaflets 450 are not properly designed, a potential nonconformance that can arise under an applied back pressure is prolapse of one of the leaflets. As seen in the dashed leaflet, if there is excess tissue at the leaflet free edge 452, a tension line "T" from the load on the leaflet may form below the free edge. During closing of the valve, the excess tissue that is above tension line "T", shown in crosshatching, may invert upon itself or prolapse as shown by arrow "P" and thereby cause transvalvular leakage. In order to remedy this problem, tension line "T" should be as coincident with free edge 452 as possible, minimizing the excess tissue above the tension line, particularly in shapes where adjacent leaflets are not able to create a coaptation section in this area.

Figure 10C:
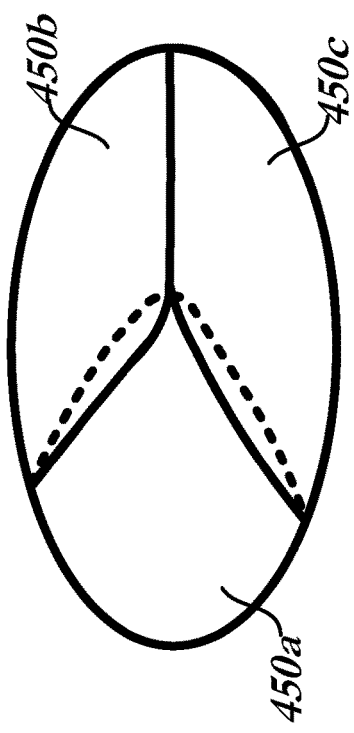
FIGS. 10B and 10C are diagrammatic end views of a valve assembly having incorrect leaflet sizing leading to regurgitation.
Figure 10B:
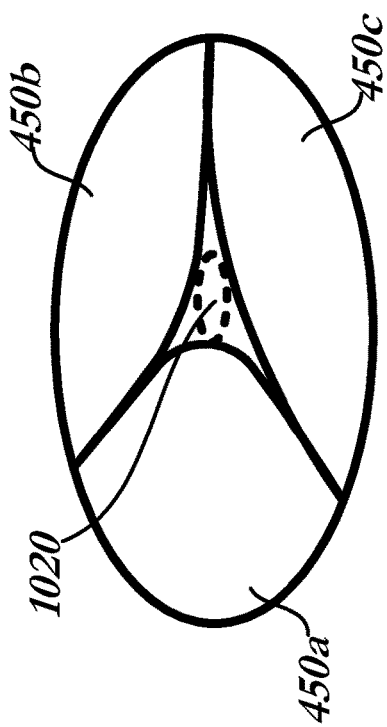
Figure 10A:
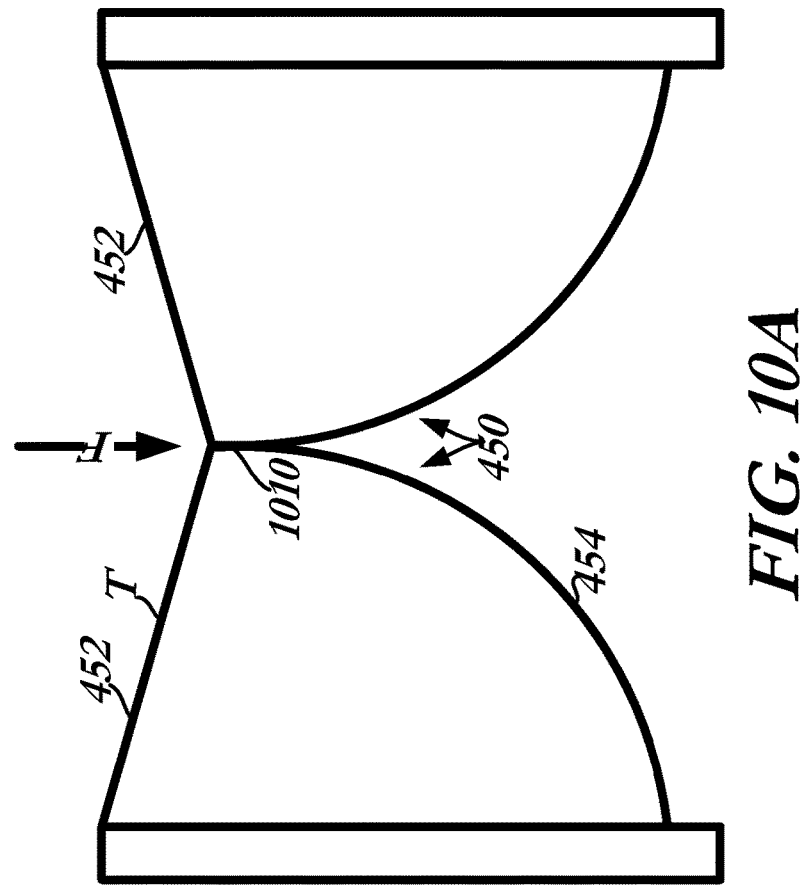
FIG. 10A is a diagrammatic cross-sectional view of a prosthetic heart valve showing leaflet coaptation along a coaptation axis.

FIG. 10A illustrates diagrammatically a valve assembly having multiple leaflets 450 showing ideal coaptation along coaptation axis 1010. A successfully functioning valve's coaptation axis 1010 will align with the force vector from the applied backpressure F. The valve assembly may also include a tension line T that will be at or near free edges 452. This configuration may prevent leaflet prolapse and regurgitation.

FIGS. 10B and 10C illustrate two examples of suboptimal sizing. In FIG. 10B, the leaflets 450 are too short and not able to coapt sufficiently with each other. The result is a central gap 1020 disposed between the leaflets. Central gap 1020 may lead to regurgitation of blood. In FIG. 10C, leaflet 450a is too long and prolapses under leaflets 450b and 450c. An elongated leaflet, such as seen in FIG. 10C, may likewise lead to regurgitation.

In addition to varying dimensions and materials, features relating to the fibers of the leaflet may also impact the function of the leaflets. Fiber orientation, for example, may make a leaflet more or less compliant and thus stretch to different extents under an applied back pressure. In the forgoing examples, tissue fibers will be discussed, although this will be understood to be merely exemplary and that the same principles may equally apply to other types of leaflets, including, for example, fabric and polymer leaflets. Fiber orientation or other property of the tissue may be determined using Polarized Light Microscopy (PLM) techniques. As seen in FIGS. 11A-C, leaflets 1150 include tissue fibers 1125 in various orientations. FIG. 11A illustrates a circumferential tissue orientation, with the tissue fibers 1125 generally traversing leaflet 1150 in alignment with the top free edge and bottom belly contour of the leaflet. FIG. 11B illustrates an axial tissue orientation having tissue fibers 1125 longitudinally arranged from the free edge to the belly of the leaflet. FIG. 11C illustrates a random tissue arrangement where the tissue fibers 1125 are not aligned with any one particular orientation.

The relative modulus of elasticity of a leaflet may also be considered in choosing the appropriate tissue. By applying a predetermined load to a tissue swatch of known diameter, the deflection of the tissue may be measured. As used herein, the term deflection refers to the distance that a structural element is displaced under a load. When matching up three tissue swatch deflection values, a maximum or minimum difference between any two swatches may be chosen.

For example, the maximum difference in deflection values between any two of the plurality of leaflets under the same load may be from about 0 to 1.0 mm under a load of 250 KPa. The maximum deflection value for each of the plurality of leaflets may be from about 1.0 to about 5.0 mm under a load of 250 KPa. For dominant fiber orientation, for example, the fiber orientation factor may be matched at any interval from 0 to 90 degrees, and the retardance (i.e., fiber density via phase difference) may be matched from 0 to 720 degrees.

In addition to fiber orientation as described with reference to FIGS. 11A-C, the density of tissue fibers 1125 may also affect the flexibility and compliance of leaflet 1150. FIGS. 11D-F illustrate three leaflets 1150 having a circumferential fiber tissue orientation. The leaflets in those figures have different fiber densities, with the leaflets in FIG. 11D having high fiber density, the leaflets in FIG. 11E having medium fiber density, and the leaflets in FIG. 11F having low fiber density.

Figure 12:
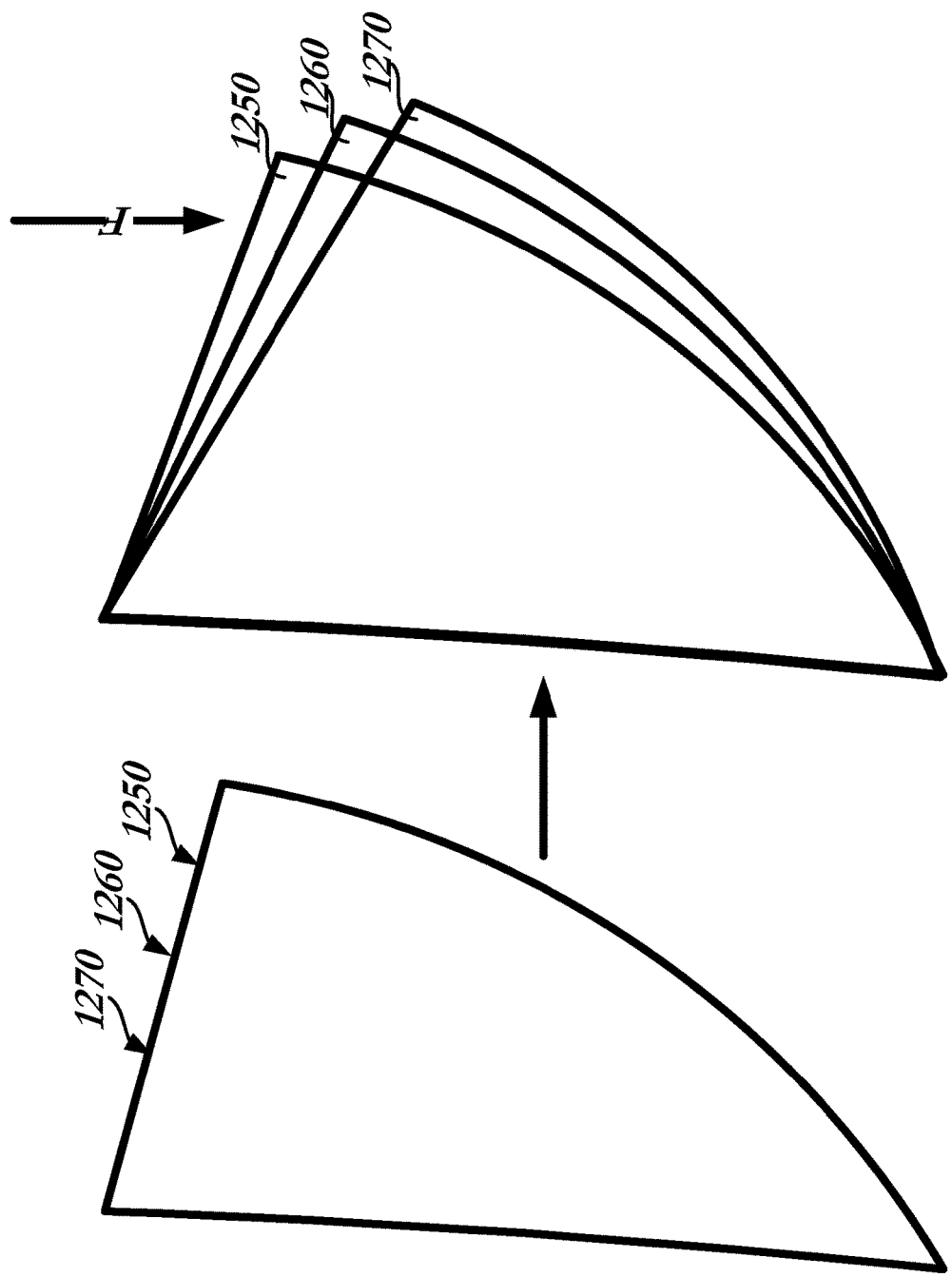
FIG. 12 shows diagrammatic views of a portion of three leaflets showing the effects of a load on the leaflets.

As discussed above, variations in fiber density and fiber orientation may affect the functioning of a leaflet. FIG. 12 illustrates three leaflets 1250, 1260 and 1270 in two states: a first state with no load applied, and a second state under a load. The illustration on the left shows that when leaflets 1250, 1260 and 1270 are not under a load, they may be of the same or similar shape or size. When the same downward force F is applied to the three leaflets, the leaflets may respond differently. As seen in the illustration on the right in FIG. 12, under force F, leaflet 1250 has been slightly deflected, leaflet 1260 has been deflected to a greater extent than leaflet 1250, and leaflet 1270 has been deflected to the greatest extent. The degree of deflection may be based on either fiber density or fiber orientation. For example, leaflets 1250, 1260 and 1270 may represent leaflets having decreasing fiber densities (e.g., the fiber density of leaflet 1250 is greatest, while the fiber density of leaflet 1270 is least). Thus, the leaflet with greatest fiber density will deflect the least, while the leaflet with the lowest fiber density will deflect the most.

Alternatively, fiber orientation may be responsible for the differences in deflection. The leaflet with circumferential fiber orientation (i.e., leaflet 1250) may be deflected the least; the leaflet with axial fiber orientation (i.e., leaflet 1260) may be deflected more; and the leaflet with random tissue fiber orientation (i.e., leaflet 1270) may be deflected to the greatest extent.

The effects of leaflet configuration and shape on the performance and function of a prosthetic valve have been addressed in the embodiments above. In addition to these examples, it will be understood that the method of leaflet attachment to the stent and/or cuff may likewise affect the performance, durability and overall function of the valve.

Figure 13A:
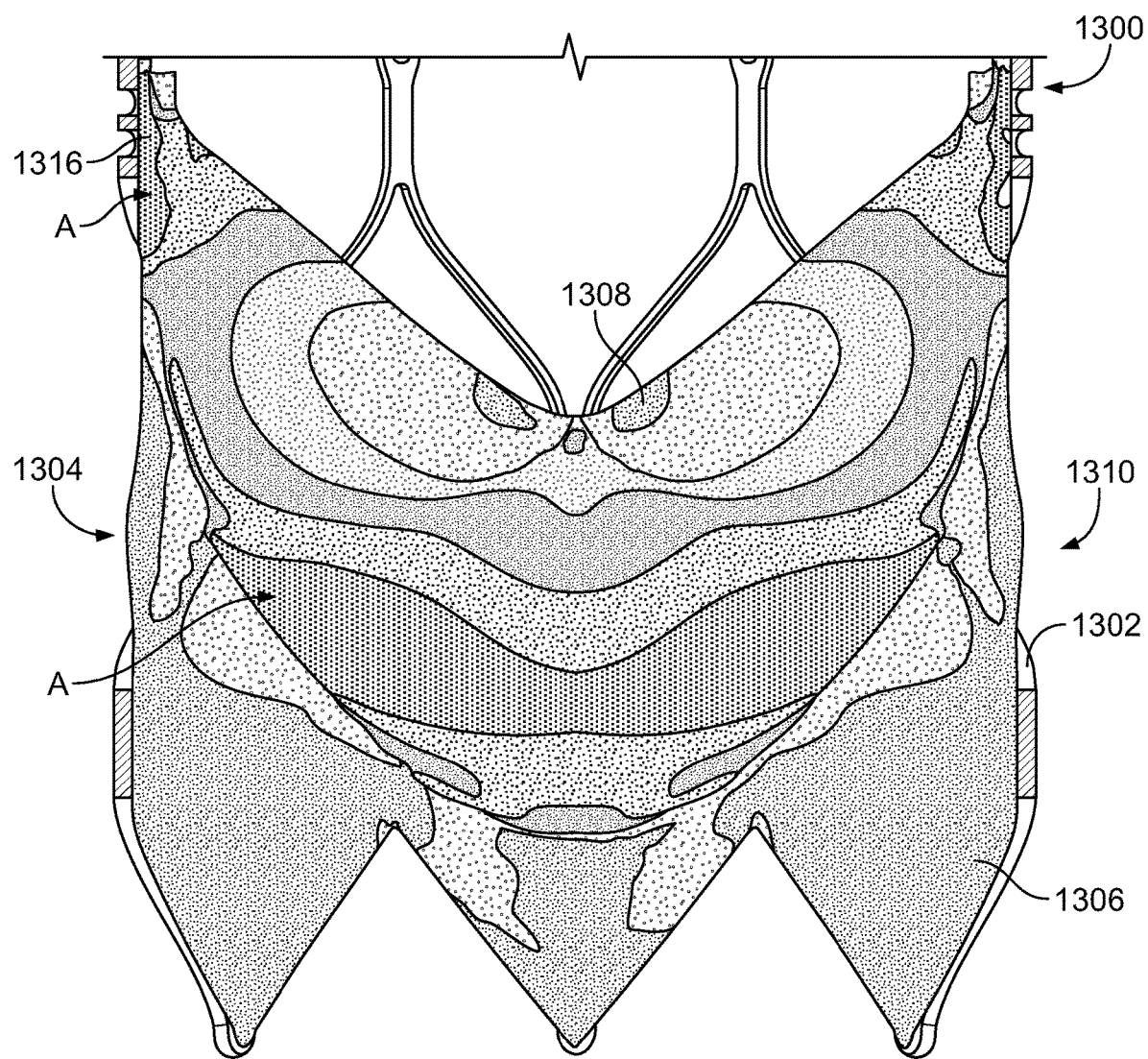
FIG. 13A is a partial side elevational view of a conventional prosthetic heart valve showing the strain distribution in the valve assembly.

FIG. 13A is a partial side view of a prosthetic heart valve 1300 having a stent 1302 and a valve assembly 1304 disposed in the annulus section 1310 of the stent. Within the heart valve 1300, leaflets 1308 are attached to cuff 1306 via sutures. Specifically, FIG. 13A shows the leaflet-cuff attachment load distribution in the valve assembly. Darker areas signify greater load. When leaflets 1308 coapt to form a closed configuration, load is transferred from the leaflet structure to the attachment points along the leaflet edge. As described in the above embodiments, these attachment points may be seen as areas A having higher loads. Moreover, when a leaflet is loaded under back pressure, high stresses are imparted on the leaflet near the commissure attachment as well as the cuff-leaflet interface.

Figure 13B:
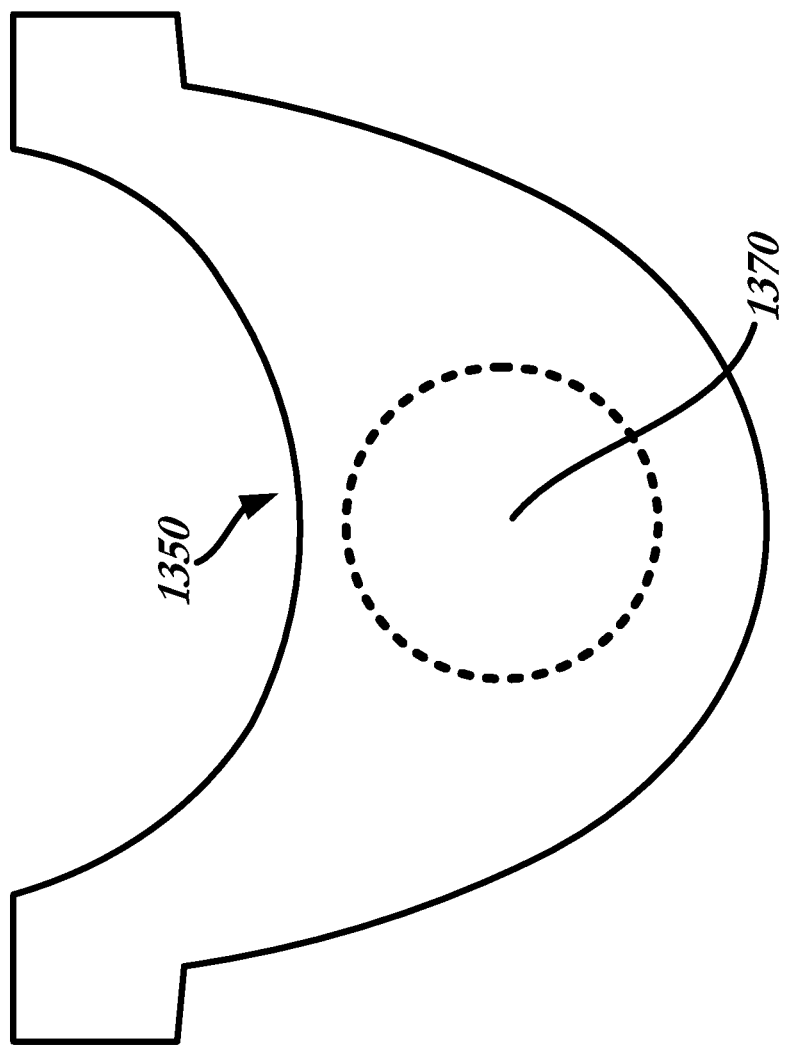
FIG. 13B is a plan view of a leaflet having an area of reduced thickness to obtain a smaller crimping profile.

Leaflet function may be improved by reducing the thickness and the crimp profile of the valve. Specifically, leaflet areas of low stress may be milled or otherwise reduced in thickness to help reduce the crimp profile. FIG. 13B illustrates a leaflet 1350 with a thinned area 1370. Though thinned area 1370 is shown as a circle in the middle of leaflet 1350, it will be understood that the thinned area can have any shape, and that leaflet 1350 may include more than one thinned area in any location where the leaflet experiences low stress, a thin belly being only one of many possible configurations. If varying the thickness of the leaflet is undesirable, then a uniform thickness leaflet may also be formed through laser milling, cryocutting, trimming or other technique, which would improve the manufacturing consistency of the valve.

Reinforcement may be utilized at the attached edge of the leaflet to increase durability. The reinforcement may include a cord, an underwire, a strip of fabric, a suture, or any other material that is capable of increasing the strength of the leaflet belly. FIGS. 14A-C illustrate various configurations of incorporating reinforcement into the leaflet.

As illustrated in FIG. 14A, leaflet 1450 may include a body portion 1460 and a foldover portion 1470. Reinforcement 1420 in the form of a cord, for example, may be disposed between body portion 1460 and foldover portion 1470. A suture S may be passed through body portion 1460, over reinforcement 1420, through foldover portion 1470 and back under the belly portion. In another example, shown in FIG. 14B, suture S may be passed through body portion 1460, through reinforcement 1420, and then through foldover portion 1470 before looping below the belly portion to the starting point. In yet another arrangement, shown in FIG. 14C, foldover portion 1470 may also wrap around reinforcement 1420, which may provide greater support for the reinforcement. In this arrangement, suture S may pass through body portion 1460, through two regions of foldover portion 1470, and then under the belly portion to the starting point. It will be understood that reinforcement 1420 may also be placed outside the foldover portion 1470.

Moreover, though the previous configurations have shown a leaflet 1450 folded over toward a cuff to form a foldover portion 1470, it will be appreciated that cuff-leaflet assembly, also referred to as a belly attachment contour, is not limited to this configuration. In other examples, the cuff-leaflet assembly includes a leaflet that is folded away from the cuff to form a foldover portion 1470 on a side of the leaflet 1450 opposite the cuff. Additionally, leaflet 1450 of the leaflet-cuff assembly need not form a foldover portion 1470 at all but may lay flat against the cuff. It is contemplated that the cuff itself may be folded over and that multiple reverse-running stitches may be utilized instead of a single stitch as described above.

Figure 15B:
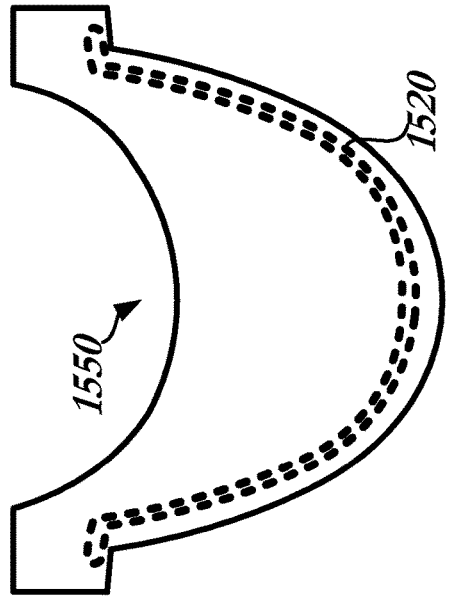
FIG. 15A-C are diagrammatic plan views of leaflets having a reinforcement region for additional support.
Figure 15A:
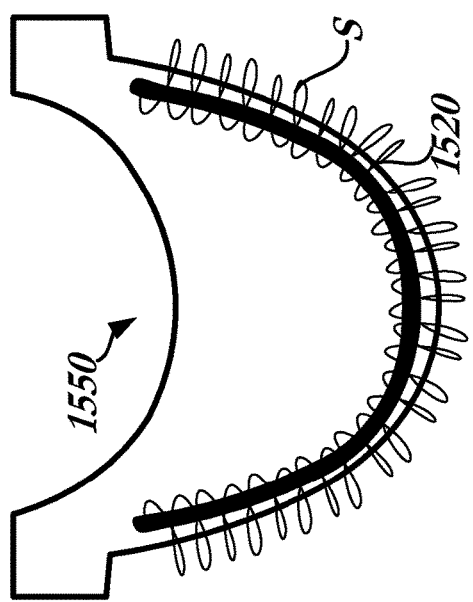

FIG. 15A illustrates one example of a leaflet 1550 having reinforcement 1520 for additional support. Reinforcement 1520 may be coupled to leaflet 1550 using a suture, an adhesive or any other method of coupling known in the art. As shown, reinforcement 1520 is coupled to the belly portion of leaflet 1550 using a suture S in a whip stitch pattern. In this example, reinforcement 1520 is made of a thickened material to provide ample support for the leaflet.

FIG. 15B illustrates a second example of leaflet 1550 having reinforcement 1520 in the form of a thin underwire that forms two rows along the belly curve of the leaflet, as shown by a dashed line. In addition to providing support for the leaflet-cuff attachment via the two rows of support, the thin underwire does not affect resheathing and loading forces and allows for a smaller crimping profile.

Figure 15C:
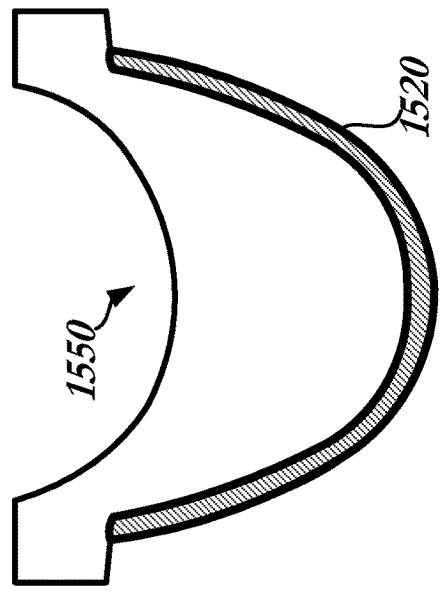

Reinforcement 1520 may also be in the form of a piece of fabric, PTFE, polyester, ultra-high molecular weight polyethylene or other materials coupled to the leaflet as seen in FIG. 15C. The fabric may be disposed along the belly of leaflet 1550 to provide a wider and more structurally sound support member for the leaflet-cuff interface than the underwire described above. The fabric may also help with tissue growth as well as sealing. The thickness of the fabric may be chosen so as not to interfere with resheathing. It will be understood that rather than fabric, reinforcement 1520 may be formed from natural tissue such as bovine, polymer or porcine tissue.

Figure 16A:
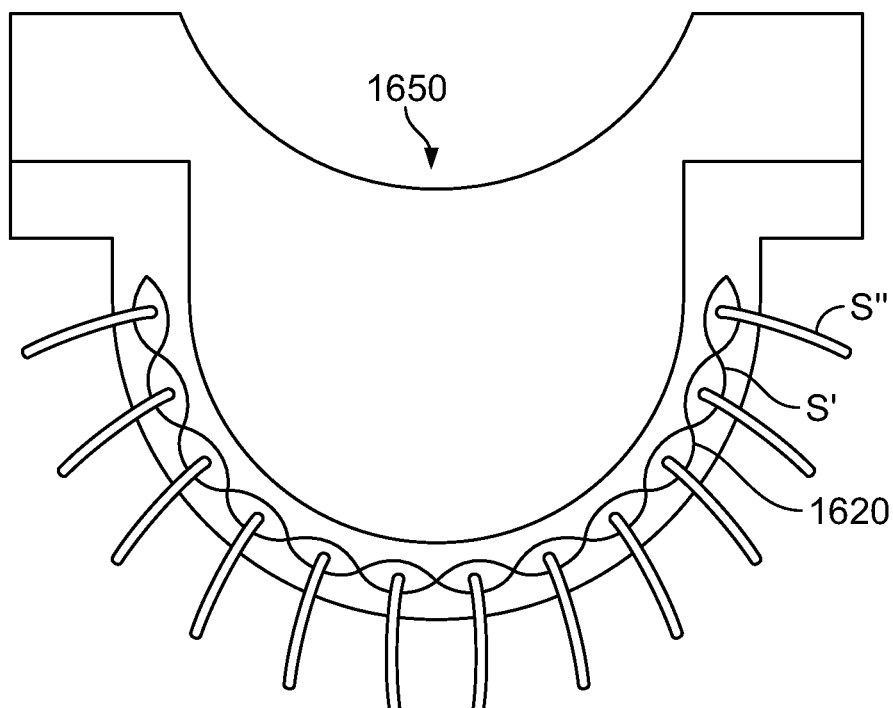
FIGS. 16A and 16B are diagrammatic views showing the attachment of the leaflet and reinforcement to a stent and/or cuff.
Figure 16B:
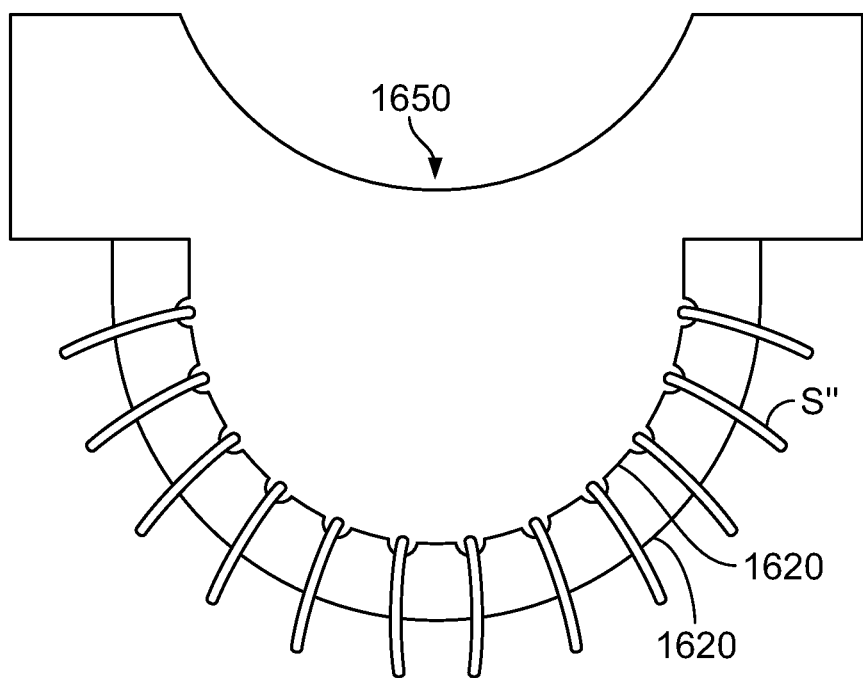

FIGS. 16A and 16B illustrate two examples of attaching the leaflet and reinforcement to the stent and/or cuff. In a first example, reinforcement 1620 is coupled to leaflet 1650 using a first stitch pattern S'. First stitch pattern S' is illustrated as a reverse-running pattern but may take on any suitable configuration. A second stitch pattern S" couples the leaflet 1650 to a stent and/or cuff (not shown). The second stitch pattern S" may wrap around or penetrate reinforcement 1620, thereby creating a more secure attachment of the reinforcement to leaflet 1650, as well as the leaflet to the stent and/or cuff.

In the second example, shown in FIG. 16B, leaflet 1650 may include one or more rows of reinforcement 1620 as described with reference to FIG. 15B. A stitch pattern S" may be used to attach leaflet 1650 to a cuff and/or stent. This example is generally sutured to act as a purse string so that the leaflet belly contour could be cinched to form a three-dimensional shape before or during attachment.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
   a collapsible and expandable stent having a proximal end, a distal end, an annulus section adjacent the proximal end, an aortic section adjacent the distal end, and a plurality of commissure features disposed on the stent;
   a collapsible and expandable valve assembly, the valve assembly including a plurality of leaflets connected to the plurality of commissure features, each of the plurality of leaflets having a body portion, a free edge adapted to coapt with free edges of adjacent leaflets, and an attachment portion having two layers opposite each free edge; and
   a plurality of discrete reinforcements, each discrete reinforcement being coupled to, and bounded by, the two layers of the attachment portion of a selected leaflet of the plurality of leaflets via a first suture pattern that passes through the two layers of the attachment portion, the first suture pattern including a plurality of continuous suture loops for each leaflet.

2. The prosthetic heart valve of claim 1, wherein the plurality of discrete reinforcements comprises at least one of a cord, wire and suture.

3. The prosthetic heart valve of claim 1, wherein the plurality of discrete reinforcements comprises a strip of fabric.

4. The prosthetic heart valve of claim 1, wherein each attachment portion includes a foldover portion.

5. The prosthetic heart valve of claim 4, wherein the foldover portion wraps around at least one of the plurality of discrete reinforcements.

6. The prosthetic heart valve of claim 1, wherein each discrete reinforcement is spaced from the free edge of the selected leaflet.

7. The prosthetic heart valve of claim 1, further comprising a cuff disposed on a surface of the stent.

8. The prosthetic heart valve of claim 7, further comprising a second suture pattern coupling each attachment portion to at least one of the stent and the cuff.

9. The prosthetic heart valve of claim 8, wherein the second suture pattern wraps around at least one of the plurality of discrete reinforcements.

10. The prosthetic heart valve of claim 8, wherein the second suture pattern pierces the reinforcement.

11. The prosthetic heart valve of claim 1, wherein each leaflet includes tabs disposed on two sides of the free edge and connected to the plurality of commissure features.

12. The prosthetic heart valve of claim 11, wherein each discrete reinforcement is bounded by the tabs of the selected leaflet.

13. The prosthetic heart valve of claim 1, wherein the first suture pattern includes reverse-running stitches.

14. A prosthetic heart valve, comprising:
- a collapsible and expandable stent having a proximal end, a distal end, an annulus section adjacent the proximal end, an aortic section adjacent the distal end, and a plurality of commissure features disposed on the stent;
- a collapsible and expandable valve assembly, the valve assembly including a plurality of leaflets connected to the plurality of commissure features, each of the plurality of leaflets having a body portion, a free edge adapted to coapt with free edges of adjacent leaflets, and an attachment portion having two layers opposite each free edge;
- a cuff disposed on a surface of the stent;
- a plurality of discrete reinforcements, each discrete reinforcement being coupled to the two layers of the attachment portion of a selected leaflet via a first suture pattern that passes through the two layers of the attachment portion; and
- a second suture pattern coupling each attachment portion to at least one of the stent and the cuff.

15. The prosthetic heart valve of claim 14, wherein the second suture pattern wraps around at least one of the plurality of discrete reinforcements.

16. The prosthetic heart valve of claim 14, wherein the second suture pattern pierces the reinforcement.

17. The prosthetic heart valve of claim 14, wherein each leaflet includes tabs disposed on two sides of the free edge and connected to the plurality of commissure features.

18. The prosthetic heart valve of claim 17, wherein each discrete reinforcement is bounded by the tabs of the selected leaflet.

19. The prosthetic heart valve of claim 14, wherein the plurality of discrete reinforcements comprises at least one of a cord, fabric, wire and suture.

20. The prosthetic heart valve of claim 14, wherein the first suture pattern includes reverse-running stitches.

* * * * *